United States Patent [19]

Lyon

[11] 4,229,603
[45] Oct. 21, 1980

[54] METHOD OF DEHYDROGENATION OF ALKYL AROMATICS TO ALKENYL AROMATICS

[75] Inventor: George W. Lyon, Midland, Mich.
[73] Assignee: The Dow Chemical Company, Midland, Mich.
[21] Appl. No.: 791,073
[22] Filed: Apr. 26, 1977

Related U.S. Application Data

[63] Continuation-in-part of Ser. No. 406,443, Oct. 15, 1973, abandoned, which is a continuation-in-part of Ser. No. 202,375, Nov. 26, 1971, Pat. No. 3,787,188.

[51] Int. Cl.² .............................................. C07C 5/38
[52] U.S. Cl. .................................................. 585/444
[58] Field of Search ..................... 260/669 R; 585/444

[56] References Cited
U.S. PATENT DOCUMENTS

| | | | |
|---|---|---|---|
| 2,461,331 | 2/1949 | Leesemann | 260/669 R |
| 2,683,180 | 7/1954 | Amos et al. | 260/669 R |

*Primary Examiner*—C. Davis
*Attorney, Agent, or Firm*—G. R. Baker

[57] ABSTRACT

A method for dehydrogenating an alkyl aromatic compound, particularly, ethylbenzene or ethyl toluene, to its corresponding vinyl aromatic derivative, styrene or methyl styrene, respectively, in which the alkyl aromatic compound and its normally attendant diluent, stream or water, are preheated to a temperature below which any substantial thermal reaction temperature of the alkyl aromatic compound occurs, viz., 450° to about 500° C., and introduced into a catalytic bed of a reactor and thereafter contacted and mixed in said catalytic bed with a quantity of steam in an amount and at a temperature to raise the alkyl aromatic compound to the catalytic dehydrogenation temperature. The steam introduced into the catalyst bed, in a ratio less than 3 to 1 to about 0.7 to 1, steam to hydrocarbon passes through the bed in heat exchange relationship to the catalyst and the reacting gases prior to contacting and mixing with the alkyl aromatic compound in the bed.

5 Claims, 2 Drawing Figures

METHOD OF DEHYDROGENATION OF ALKYL AROMATICS TO ALKENYL AROMATICS

CROSS-REFERENCE TO RELATED APPLICATIONS

The present application is a continuation-in-part of my previous application Ser. No. 406,443 filed Oct. 15, 1973, and now abandoned which in turn is a continuation-in-part of my earlier filed application Ser. No. 202,375 filed Nov. 26, 1971, now U.S. Pat. No. 3,787,188, granted Jan. 22, 1974.

BACKGROUND OF THE INVENTION

The dehydrogenation of alkyl aromatic compounds is conventionally carried out on a commercial scale by passing the alkyl aromatic compound at an elevated temperature through a zone containing a selective dehydrogenation catalyst. Steam is mixed with the alkyl aromatic compound both as a diluent and as a source of heat to raise the alkyl aromatic compound to the dehydrogenation temperature and supply the endothermic heat required for the reaction. Since dehydrogenation also occurs thermally in the absence of a catalyst and this dehydrogenation is non-selective, it is common practice to preheat the alkyl aromatic compound to only about 450° to 500° C., a temperature whereat little, if any, thermal dehydrogenation will occur, and use steam to raise the temperature to the reaction temperature just prior to entry of the admixture into the catalyst bed. Sufficient steam must be added to not only raise the mass to reaction temperature but also to supply the endothermic heat of reaction as the reaction proceeds throughout the bed. The balancing of the steam, both quantity and temperature, to achieve good yields and high selectivities (the percentage of consumed alkyl aromatic compound converted to desired product) has prompted industry to employ two and more often three or more weights of steam per weight of alkyl aromatic compound. Over the years various schemes have been proposed to the end of reducing the steam volume introduced into the reactor. One such scheme which has been implemented on a commercial scale is the heated case reactor as exemplified by Amos et al., U.S. Pat. No. 2,683,180. In this scheme, steam is passed around the catalyst bed in a countercurrent flow to heat the bed and then the steam is mixed with the incoming alkyl aromatic compound. The teaching in the reference patent uses a 3 to 1 steam to alkyl aromatic ratio (S/HC) in the heated case scheme and achieves better results than using the same ratio without heated case, a yield of 86.5 percent versus 79.6 percent. This same reference discloses use of a jacketed reactor heated with flue gas. Similar results were obtained as when the steam was used as compared to unheated case reactors.

Another scheme employed by the industry is the intermediate introduction of steam, best exemplified by Kindler et al., U.S. Pat. No. 3,660,510. This patent discloses 90+ percent yields using three reactors and introducing steam intermediate to provide a 1 to 3 steam ratio in reactor 1; a 2 to 3 steam ratio in reactor 2 and a 3 to 3 steam ratio in reactor 3. This reference illustrates the stepwise conversions when using less than 1 to 1 ratios; i.e., at 1 to 3 conversion is 18 percent, when 2 to 3 is an additional 15–18 and finally at 1 to 1 is an additional 10–12 percent and demonstrates the effect of depending solely on the heat of the steam mixed with the alkyl aromatic to supply the endotherm.

Each of these schemes establishes a process for employing less steam than previous processes or at least obtaining better yields with equivalent steam quantities.

A still further scheme suggested to the industry is that disclosed in Leesemann, U.S. Pat. No. 2,461,331. The patent teaches introducing the alkylaromatic through several distributors located at various levels in the catalyst bed and introducing steam into the bed from the bed surface. The ratio of steam to hydrocarbon is very high throughout a major portion of the bed and generally is 5–40 to 1 even at the exit. Although the reference suggests that a 1 to 1 steam ratio at the outlet can be achieved the early ratios in the bed are higher, i.e., 5–40 to 1 steam to hydrocarbon. Further, the steam is at its highest ratio to hydrocarbon when it is in the greatest ratio. Finally, the process admits of cumbersome equipment and a procedure in which the hottest temperatures are associated with the minimum hydrocarbon.

It is an object of the present invention to provide a scheme which provides an alternative method for achieving improved yields, with low steam ratios. These and other objects will be evident to those skilled in the art to which the invention pertains.

SUMMARY OF THE INVENTION

This invention relates to a method of dehydrogenating alkyl aromatic hydrocarbons to the corresponding vinyl aromatic derivatives in a catalytic reactor having separate inlet means for a reactant stream of a component to be dehydrogenated and for a heat maintaining fluid stream such that the streams are mixed only in the presence of a catalyst. The alkyl aromatic-containing streams flow axially through the catalyst bed and the heating fluid stream flows radially into and then axially through the catalyst bed. The heating fluid stream is introduced into the catalyst bed in a manner to exchange some of its heat to the bed prior to introduction into intimate contact with the bed.

DETAILED DESCRIPTION OF THE INVENTION

Figure 2:
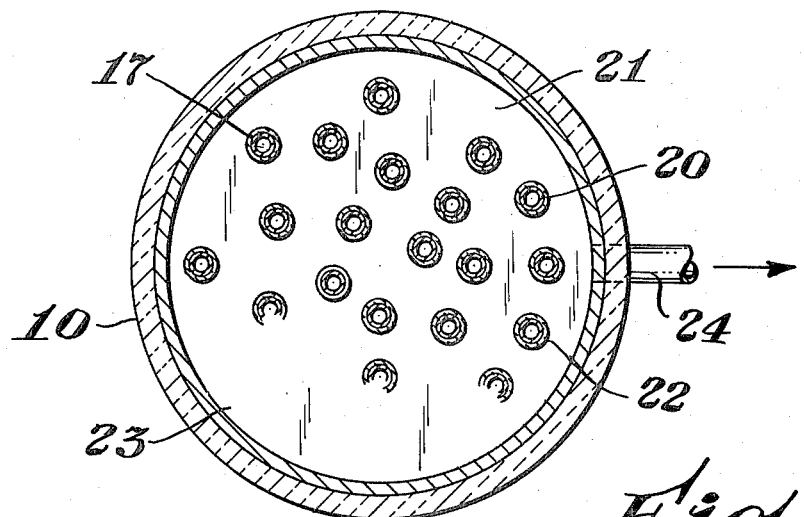
FIG. 2 is a cross-section along lines 2–2 of FIG. 1.
Figure 1:
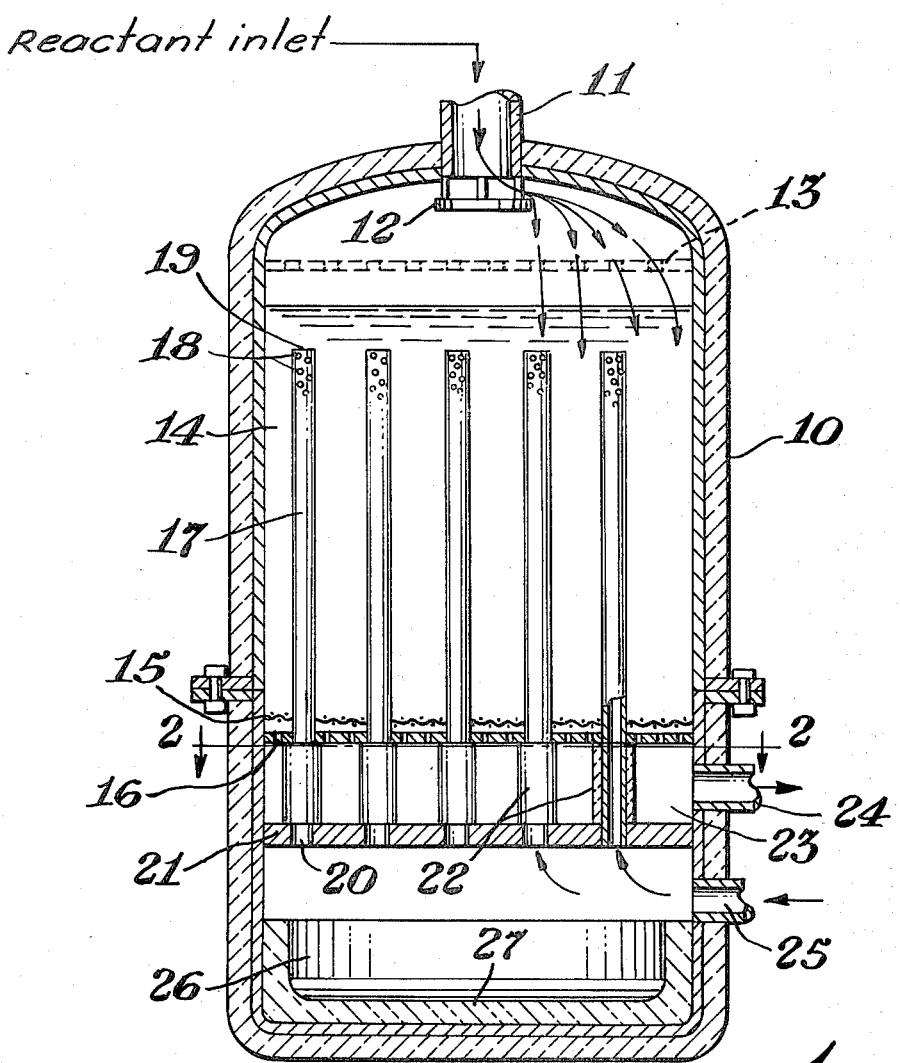
FIG. 1 is an elevation, partly in section, of the reactor.

Referring to the drawing, FIG. 1, 10 is a reactor shell having at its top a flanged inlet port 11. Shell 10 preferably has an insulating coat (not shown) to minimize loss of heat by radiation. A deflector 12, attached to shell 10 is situated at the base of and attached to the walls of port 11. Beneath the deflector, optionally, is a foraminous distributor 13. A catalyst zone 14, located between a tube sheet or a support plate 16 and below inlet 11 extends from a position below distributor 13, to a screen 15 which has openings small enough to retain the catalyst. Screen 15 is supported on a perforated plate or tube sheet 16, which can have up to 50 percent of its surface area open. Plate 16 preferably abuts tightly against the inner periphery of shell 10 and can, if desired, be welded to the shell. Through plate 16 and screen 15 protrude a plurality of tubes 17, each of which has a plurality of openings 18, at its upper surface and an imperforate top 19 and opening 20 at the base. Openings 18 are fine enough to prevent entry of catalyst or if the catalyst is finely divided, the openings are covered with a screen of mesh size such that catalyst is retained in the bed. The tubes serve as an inlet for a component into the reactor. Tubes 17 are mounted in a single tube sheet 21. Each tube 17 can, if desired, contain an external insulating sleeve 22, extending from tube sheet 21 to the catalyst support plate 16, to minimize heat transfer to passageways 23. Passageways 23 serve as reservoir manifold for reacted components leading to flanged outlet 24. Near the base of the reactor is another flanged inlet port 25 leading to a reservoir 26 for a feed component into the reactor. The base of inlet port can be insulated either internally or externally against heat loss, the internal insulation being shown at 27.

The insulating sleeves 23 and insulating base material 27 can be made of porcelain, fire brick, asbestos or any other heat insulating material which will not effect an unwanted reaction with a feed ingredient or a desired ingredient obtained in the reaction.

The single tube sheet arrangement of the reactor minimizes the stresses due to expansion and contraction of metal, as compared with a double tube sheet reactor. The operation of the reactor is described with reference to dehydrogenation of ethylbenzene to styrene, although it is to be understood that any other catalytic reaction can be performed therein. Ethylbenzene preheated to about 450° to about 625° C. is fed into the reactor as vapor through port 11. Steam at a temperature of about 650° to about 1000° C. is fed through port 25 in a ratio of about 0.8 to 2 pounds per pound of ethylbenzene. The steam enters insulated reservoir 26, passes through openings 20 and tubes 17 and enters the bed 14 through openings 18, where it commingles with ethylbenzene. Tubes 17, which carry the hot steam will also transfer heat by conduction to the catalyst area surrounding the tubes. Thus, with proper size and spacing it is possible to maintain the entire catalyst bed at reaction temperature, even though the reaction itself is endothermic. Reaction temperature is maintained in the range of 575° to 675° C. Preferably, the tubes 17 have inner diameters of from about 2 to about 6 inches and are spaced from about 1 to about 3 tube diameters apart. The spacing is preferably about equidistant, so as to maintain a relatively uniform temperature profile in a catalyst bed cross-section. Thus, the ethylbenzene temperature is not raised to dehydrogenation temperature until it is in contact with a dehydrogenation catalyst. In this manner conversion of ethylbenzene to unwanted side reaction products is greatly minimized. Further, it has been found that temperatures at which ethylbenzene is decomposed in the presence of metal surfaces can be readily attained in the catalyst bed without appreciable decomposition of the ethylbenzene with and greater tendency to dehydrogenate to styrene. The reaction mixture passes through the catalyst bed 14, screen 15 and screen support 16 into passageway 23 and out of the reactor through outlet 24.

For other reactions in which the temperature and/or catalytic dehydrogenation conditions need not be controlled as closely as that needed for preparing styrene, as described, the steam can be fed through port 11 and preheated (e.g., below thermal cracking temperatures) hydrocarbon without steam or diluent can be fed through inlet port 25. Mixing of the steam and hydrocarbon vapors will not be effected until the catalyst bed is reached. That is, the hydrocarbon is not at a reaction temperature or reaction conditions until it enters the bed and is therein mixed with the steam. Otherwise the procedure for dehydrogenating ethylbenzene is the same as above described.

Catalysts which can be used for dehydrogenating ethylbenzene to styrene are well known. Preferred is a self-regenerative catalyst. A representative catalyst is one which contains about 65 to about 90 weight percent ferric oxide, about 2 to about 5 percent chromium oxide and about 10 to about 35 percent potassium carbonate and the remainder being binders, which may be partially removed in a calcining step. Included but not limited thereto are catalysts described in U.S. Pat. Nos. 3,084,125; 3,361,683; 2,395,875; 2,395,876; 2,408,140; 2,414,585; 2,461,147 and U.S. Pat. No. Re. 22,800. Any other dehydrogenation catalyst is operative.

The reactor can be made of a variety of materials of construction including 18/8 type stainless steels, low nickel high chrome stainless steels of the ASI 400 series, the various clad stainless steels, ceramic lined steels including the stainless steels mentioned above, and if temperatures of reaction permit, carbon steels.

The present invention also relates to a method for dehydrogenating alkyl aromatic compounds to their corresponding vinyl derivatives over a dehydrogenation catalyst, by feeding a mixture of the alkyl aromatic compound with a portion of its normally attendant diluent, steam and/or water, which mixture has been preheated to a temperature near but below the thermal dehydrogenation temperature, i.e., 450°–500° C., into a catalyst bed maintained at about 575°–675° C. and on initial contact with the catalyst the mixture is heated and mixed with additional steam to both further dilute the alkyl aromatic compound and to heat it and its diluent to the dehydrogenation reaction temperature all in the presence of the selective dehydrogenation catalyst. In accordance with the present invention, the incoming alkyl aromatic compound and its diluent are not heated to reaction temperature prior to contact with the catalyst and the heating is done simultaneously with dilution by the steam at the surface and interior of the bed. This is in contrast to the prior art, as exemplified by Amos et al. and Kindler et al., each of which mixes added steam and alkyl aromatic compounds prior to contact with the catalyst, thus the alkyl aromatic compound is subjected to conditions under which non-selective reactions occur forming benzene, toluene and carbon, preferentially to the formation of the vinyl derivative. This occurs in Kindler et al., even though they limit the time the alkyl aromatic is at this temperature before contact with the catalyst. Thus, the present invention provides a procedure for reducing side reactions and by-product formation which reduce the efficiency of the process. In addition, the present process employs the heat in the steam before mixture with the hydrocarbon to supply some of the endothermic heat of reaction as the reactants pass through the catalyst bed. This is accomplished by introducing the steam into tubes which extend into the catalyst bed and terminate within the bed. The terminus of each tube is provided with holes allowing the steam to enter the bed and mix with the incoming alkyl aromatic. Such a configuration for the introduction of the added steam insures the bed throughout will be at or near the optimum temperature for the most efficient dehydrogenation of the particular alkyl aromatic compound while simultaneously reducing the mass of added steam into the reaction mass to maintain this temperature. Thus, good yields are obtained with low steam to hydrocarbon ratios.

In a typical run, the reactor is filled to a height just above tubes 17 so as to cover the tube with a catalyst containing about 88 percent ferric oxide, about 10 percent potassium carbonate and about 2 percent chromic oxide (Shell 105). A mixture containing about 81.3 percent by weight of ethylbenzene and about 18.7 percent by weight of steam, preheated to about 560° C. is fed continuously into the reactor through port 11. Sufficient steam at about 900° C. is fed into the reactor through port 25 to provide a total steam:ethylbenzene ratio of 1 to 1. Flow rates are adjusted so that the temperature of the effluent from outlet 24 is 595° C. The conversion is about 41 percent per pass and the selectivity is 92-94 percent based on the ethylbenzene converted.

If steam at about 827° C. is fed into port 25, it is necessary to employ a steam-ethylbenzene ratio of about 1.28 to 1 in order to maintain an effluent temperature of about 595° C. The conversion and selectivity per pass, however, will be about the same as described above. The ethylbenzene feed rate into the reactor can vary between about 25-50 pounds per cubic foot of catalyst without major effect on the conversion or selectivity per pass.

From the following table, wherein the lb-mol of steam, the steam temperature and steam to hydrocarbon ratios are set forth to achieve ca., 41 percent conversion with maximum yields, it will be apparent that less steam as well as more optimum reaction temperatures can be employed in comparison with Amos et al. and Kindler et al. (supra).

Assume: Feed 369 lb-mol ethylbenzene feed (39100 lbs)
Feed 500 lb-mol H₂O (9000 lbs)
(a 1 to 4 steam to hydrocarbon ratio weight basis)
Reactor temperatures: 595° C. outlet,
56-° C. inlet.

| Steam Temperature | lb mol Added | Total Ratio S/HC |
|---|---|---|
| 650 | 4,302 | 2.23 |
| 700 | 3,324 | 1.78 |
| 800 | 2,498 | 1.4 |
| 827 | 2,238 | 1.28 |
| 900 | 1,672 | 1.0 |
| 1000 | 804 | 0.62 |

In a series of runs, ethylbenzene was fed to a reactor vessel filled with an iron oxide self-regenerative catalyst, i.e., Shell 105, and steam was fed into the interior of a body of catalyst at a point near the point of introduction of the ethylbenzene. The total steam ratio to hydrocarbon was 2 to 1. The ethylbenzene was preheated to the indicated temperature and the steam introduced had the temperature set forth. The liquid hourly space velocity was 1.0, the pressure 5.0 psig. Representative data collected is reported in the following table.

| Run | Steam Temp. °C. | Ethylbenzene-Steam Mixture* Temp. °C. | % Conv. Ethyl-Benzene | % Styrene Select. |
|---|---|---|---|---|
| | 755 | 530 | 47.9 | 94.1 |
| | 740 | 530 | 44.3 | 95.2 |
| | 775 | 535 | 40.9 | 95.2 |
| | 675 | 560 | 32.9 | 95.9 |
| | 785 | 540 | 48.8 | 92.4 |
| | 800 | 535 | 52.8 | 91.4 |
| | 810 | 540 | 54.4 | 92.5 |
| | 820 | 540 | 60.1 | 90.3 |

*Inlet temperature of feed stream prior to mixing with added steam in bed.

When this data is compared to a process wherein the steam and hydrocarbon are premixed, it is apparent more advantageous results are obtained. The comparative runs were made by mixing steam at a temperature and in an amount such that when mixed with preheated ethylbenzene steam (450°-500° C.) there was obtained a 2 to 1 steam to hydrocarbon ratio and an inlet temperature to the bed of catalyst as noted. All other conditions were the same as the previous example.

| Run | Inlet Temp.* °C. | Outlet Temp. | % EB Conv. | % Styrene Select. |
|---|---|---|---|---|
| | 625 | 559 | 33.6 | 95.1 |
| | 608 | 546 | 29.0 | 96.2 |
| | 631 | 570 | 39.7 | 94.1 |
| | 642 | 577 | 40.1 | 94.1 |
| | 655 | 584 | 54.0 | 89.7 |
| | 663 | 596 | 55.1 | 89.6 |
| | 670 | 590 | 58.0 | 87.4 |

*Temperature of stem and ethylbenzene just prior to entering bed.

Note that employing the method of the present invention both higher conversions and higher selectivities are achieved and maintained as the temperature is raised as compared to the pre-mixing of steam and hydrocarbon as practiced by the prior art. The reaction has been specifically described as useful for dehydrogenating ethylbenzene to styrene. However, the method is particularly useful for adiabatic dehydrogenations of other alkyl aromatics including isopropylbenzene, diethyl benzene, ethyl toluene, diethyl toluene, ethyl xylene, ethyl naphthalene and other such aromatic compounds having from 1 to 3 alkyl groups of which 1 to 2 contain 2-3 C atoms, and the remaining groups are methyl groups.

I claim:

1. A method for dehydrogenating an alkylbenzene compound having from 1 to 3 alkyl groups attached to a benzene nucleus of which 1 to 2 alkyl groups contain 2-3 C atoms comprising feeding said alkylbenzene compound at a temperature of 450°-500° C. through the inlet port of a reactor, feeding stream at a temperature of 650° to about 1000° C. into the interior of a fixed bed of dehydrogenation catalyst, said stream flowing in a countercurrent manner to said flow of alkylbenzenes in heat exchange relationship in said bed prior to introduction into said bed, said point of introduction being just below the point of introduction of the alkylbenzene compound into said bed, said steam being supplied in sufficient quantity to maintain the mixture, at a temperature of about 575° to 675° C. upon mixing the alkybenzene and steam in said catalyst bed, passing the mixture through said catalyst bed and withdrawing reacted effluent from the reactor, the total steam to hydrocarbon ratio weight to weight basis, being less than about 3 to 1, to about 0.7 to 1 each respectively.

2. The method of claim 1 in which ethylbenzene is dehydrogenated to styrene.

3. The method of claim 1 in which ethyl toluene is dehydrogenated to vinyl toluene.

4. The method of claim 1 in which isopropyl benzene is dehydrogenated to alpha methyl styrene.

5. The method of claim 1 in which diethylbenzene is dehydrogenated to a mixture of divinyl benzene and ethyl vinylbenzene.

* * * * *

UNITED STATES PATENT AND TRADEMARK OFFICE
CERTIFICATE OF CORRECTION

PATENT NO. : 4,229,603
DATED : October 21, 1980
INVENTOR(S) : George W. Lyon

It is certified that error appears in the above-identified patent and that said Letters Patent are hereby corrected as shown below:

In the Abstract, line 6, correct the word "stream" to --steam--.

Col. 4, line 40, correct the word "compounds" to --compound--.

Col. 5, line 35, correct the number "56-°" to --560°--.

Col. 6, line 26, in the footnote to table, correct the word "stem" to --steam--.

Col. 6, line 46, correct the word "stream" to --steam--.

Col. 6, line 48, correct the word "stream" to --steam--.

Col. 6, line 54, correct the word "alkybenzene" to --alkylbenzene--.

Signed and Sealed this

Seventeenth Day of March 1981

[SEAL]

Attest:

RENE D. TEGTMEYER

Attesting Officer

Acting Commissioner of Patents and Trademarks